United States Patent [19]
Dirks et al.

[11] Patent Number: 6,135,106
[45] Date of Patent: *Oct. 24, 2000

[54] CPAP PRESSURE AND FLOW TRANSDUCER

[75] Inventors: Aaron J. Dirks, Overland Park; Jeffrey M. Waldo, Stilwell, both of Kans.

[73] Assignee: Nellcor Puritan-Bennett, Inc., Pleasanton, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/916,879

[22] Filed: Aug. 22, 1997

[51] Int. Cl.[7] .................................................. A61M 16/00
[52] U.S. Cl. ............................... 128/204.23; 128/204.21; 128/205.23; 128/204.18
[58] Field of Search ................... 128/204.23, 204.18, 128/204.21, 204.22, 205.23, 207.14, 203.12, 203.15; 60/520, 532; 73/861.74, 861.52; 600/538

[56] References Cited

U.S. PATENT DOCUMENTS

| | | |
|---|---|---|
| 4,047,521 | 9/1977 | Kramer et al. ......................... 600/538 |
| 4,984,158 | 1/1991 | Hillsman .............................. 128/205.23 |
| 5,167,506 | 12/1992 | Kilis et al. .......................... 128/205.23 |
| 5,363,842 | 11/1994 | Mishelevich et al. ............. 128/205.23 |
| 5,379,650 | 1/1995 | Kofoed et al. ........................ 73/861.52 |
| 5,517,983 | 5/1996 | Deighan et al. .................... 128/204.23 |
| 5,522,382 | 6/1996 | Sullivan et al. .................... 128/204.23 |
| 5,551,419 | 9/1996 | Froehlich et al. .................. 128/204.23 |
| 5,577,496 | 11/1996 | Blackwood et al. ............... 128/204.23 |
| 5,803,066 | 9/1998 | Rapoport et al. ................... 128/204.23 |

Primary Examiner—John G. Weiss
Assistant Examiner—V. Srivastava
Attorney, Agent, or Firm—Hovey, Williams, Timmons & Collins

[57] ABSTRACT

A continuous positive airway pressure (CPAP) apparatus for treatment of sleep apnea stores data indicating patient compliance with the prescribed mode of use. The apparatus includes a tubular probe positioned transversely in the conduit between the blower and nose mask. The probe tip is configured for creating a varying pressure across in the probe in response to varying air flow thereacross indicative of patient respiration. A pressure sensor connected to the probe produces signals representative of the varying air pressure. Compliance data, derived from the pressure sensor signals and representative of the patient's use of the apparatus, are stored for subsequent analysis.

23 Claims, 1 Drawing Sheet

CPAP PRESSURE AND FLOW TRANSDUCER

RELATED APPLICATIONS

Not applicable.

FEDERALLY SPONSORED RESEARCH OR DEVELOPMENT

Not applicable.

MICROFICHE APPENDIX

Not applicable.

BACKGROUND OF THE INVENTION

1. Field of the Invention

The present invention relates to the field of respiratory treatment. In particular, the invention is concerned with a continuous positive airway pressure (CPAP) apparatus for treatment of sleep apnea which stores data indicating patient compliance with the prescribed mode of use.

2. Description of the Prior Art

In the treatment of sleep apnea and other conditions, the use of continuous positive airway pressure (CPAP) is often prescribed in order to provide an air splint to a patient's airway passages for maintaining an open airway during sleep thereby preventing or minimizing sleep apnea events. In order to evaluate the effectiveness of CPAP treatment, it can be important for the evaluator to know the degree to which the patient has complied with the prescribed mode of treatment. That is, it is important to know whether the patient has used the CPAP device as prescribed.

Some BIPAP (bi-level positive air pressure) devices have included a pair of probes coupled with a flow sensor for measuring air flow (necessary for triggering the two pressure levels) and a third probe coupled with a pressure sensor for measuring static air pressure in order to control operations. These sensing arrangements add to manufacturing cost and operational complexity.

SUMMARY OF THE INVENTION

The present invention solves the prior art problems discussed above and provides a distinct advance in the state of the art. In particular, the CPAP pressure and flow transducer hereof provides a reliable yet simple and inexpensive way to derive patient compliance data.

The preferred CPAP apparatus includes a blower unit, a nose mask and a conduit therebetween, and further includes a controller for controlling the operation of the apparatus including the selected air pressure produced by the blower provided to the patient. The controller also includes a sensing assembly for sensing air flow direction in the conduit, such being indicative of patient respiration and thereby indicative of patient use of the apparatus.

The preferred sensing assembly includes a tubular probe having a probe tip positioned in the conduit and configured for producing a varying pressure in the probe that varies according to air flow direction in the conduit. A pressure sensor coupled with the probe senses the varying pressure and produces pressure signals representative thereof. A signal processor analyzes the pressure signals and derives air flow direction, magnitude and static pressure therefrom which are further processed and stored as compliance data in the controller. Other preferred aspects of the present invention are disclosed herein.

DETAILED DESCRIPTION OF THE PREFERRED EMBODIMENT

Figure 1:
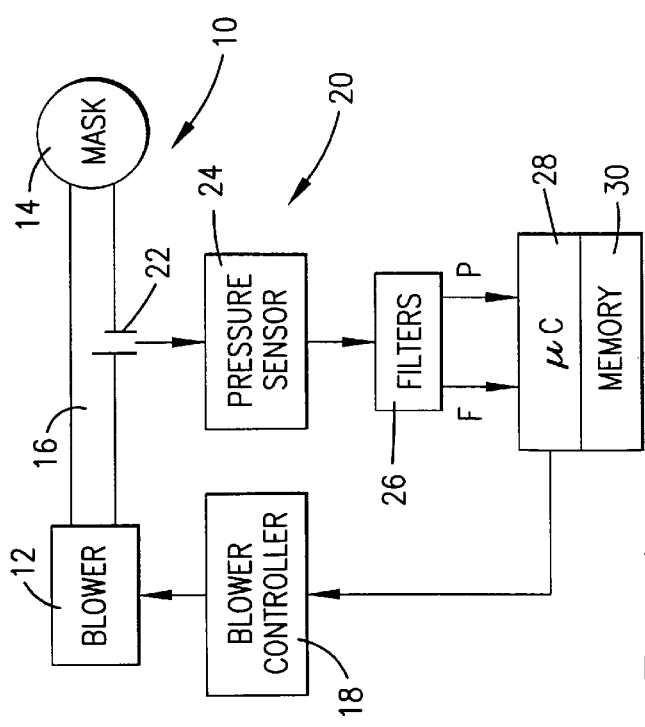
FIG. 1 is a block diagram of the preferred CPAP apparatus in accordance with the present invention.

FIG. 1 illustrates preferred CPAP apparatus 10 in accordance with the present invention. Apparatus 10 includes blower 12, nose mask 14, conduit 16 interconnecting blower 12 and mask 14, blower controller 18 and sensing assembly 20. In the preferred embodiment, components 12–18 are conventional in nature as found in typical CPAP devices operable for maintaining a selected continuous positive airway pressure to a patient wearing mask 14 in order to treat sleep apnea and other conditions. Sensing assembly 20 includes probe 22, pressure sensor 24, signal filter 26 and microcontroller 28 with associated memory 30.

Figure 2:
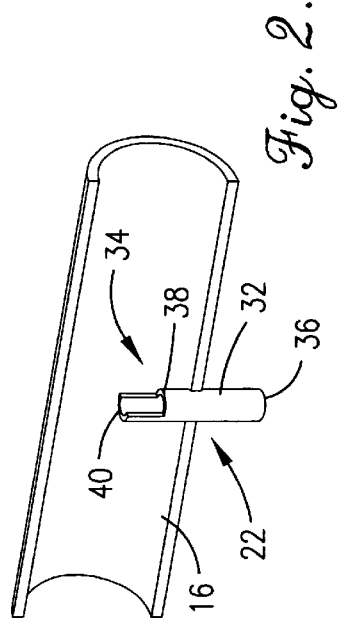
FIG. 2 is a pictorial view of the preferred probe positioned in the conduit of FIG. 1 in partial section.

As best viewed in FIG. 2, tubular probe 22 includes tube wall 32 presenting a circular cross section and configured to present probe tip 34 and opposed, connection end 36. A portion of probe 22 is positioned in conduit 16 transverse to the air flow therethrough with probe tip 34 positioned therein and connection end 36 positioned outside conduit 16 for connection to pressure sensor 24. Probe tip 34 includes interior end 38 with a portion of tube wall 32 extending therefrom to present arcuate wall extension or vane 40.

In the preferred embodiment, probe 22 is oriented so that vane 40 is positioned adjacent the upstream side of interior end 38 when the air flow direction is from blower 12 toward mask 14. This would occur during inhalation by a patient wearing mask 14. With air flow toward mask 14, vane 40 causes a reduction in the air pressure at interior end 38 resulting in a varying air pressure in probe 22 that varies according to air flow magnitude and direction. Conversely, air flow through conduit 16 away from mask 14, which corresponds to patient exhalation, causes an increase in pressure increase at interior end 38 resulting in a varying air pressure at interior end 38. That is, probe tip 34 produces varying pressure in probe 22 that varies in accordance with air flow direction and also in accordance with air flow magnitude in conduit 16. This varying air pressure is provided by way of connection end 36 to pressure sensor 24 connected thereto.

Figure 3:
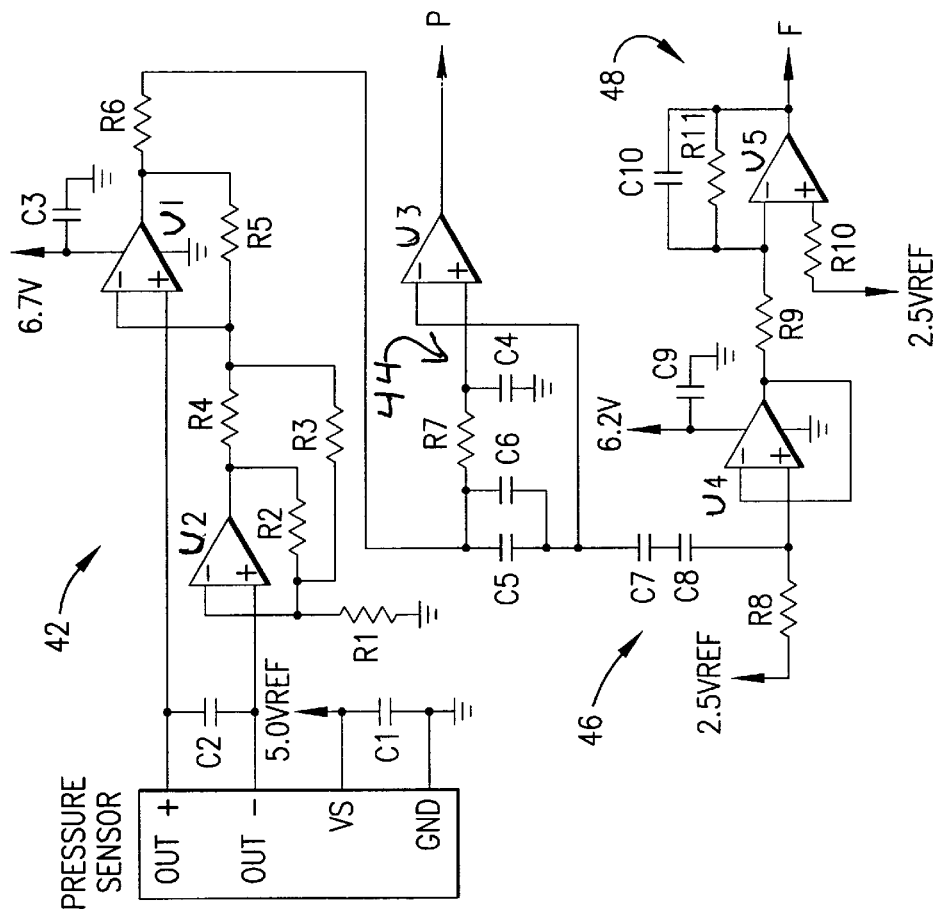
FIG. 3 is an electrical schematic diagram of the pressure sensor and signal filters of FIG. 1.

FIG. 3 is an electrical schematic illustrating pressure sensor 24 and filter 26. Pressure sensor 24 is preferably Model SM5657 available from Silicon Microstructures and produces an electrical output at terminals OUT+ and OUT– representative of the pressure in probe 22. Capacitor C1 (1.0uF) is connected across terminals VS and GND with VS also connected to a reference voltage of 5.0 V and terminal GND connected to ground. Sensing assembly 20 also includes conventional circuitry (not shown) for providing other supply and reference voltages at 6.2 V and 2.5 V Ref.

The output signals of sensor 24 are connected to filter 26 which initially provides signal amplification with a gain of about 428 using amplifier circuit 42 including amplifiers U1 and U2 (Type LT1078) as illustrated in FIG. 3. Specifically, capacitor C2 (0.22uF) is connected across terminals OUT+ and OUT– which are also connected respectively to the positive input terminals of amplifiers U1 and U2. The negative input terminal of U2 is connected to grounded resistor R1 (10K), resistor R2 (10K) also connected to the output of U2 and to resistor R4 (10K), and to resistor R3 (26.7K) which is connected to the other side of R4 and to the negative input terminal of U1. Resistor R5 (10K) interconnects the output of U1 with the negative input terminal thereof. Supply voltage at 6.2 V is connected to U1 and to capacitor C3 (0.1uF). The output from U1 is provided by way of resistor R6 (390K) as the output from amplifier circuit 42.

Filter 26 further includes low pass filter 44, high pass filter 46 and low pass filter 48. The output from amplifier circuit 42 is connected to low pass filter 44 having a cutoff frequency of about 2.9 Hz. This provides a relatively long time constant for filtering the high frequency components in the pressure signal provided by sensor 24 in order to produce signal P representative of the static pressure in conduit 16. In particular, the negative input from amplifier circuit 42 is provided by way of resistor R7 (390K) to the positive input terminal of amplifier U3 (Type LT1078). Grounded capacitor C4 (0.1uF) is also connected to this terminal. Capacitors C5 (0.1uF) and C6 (0.1uF) are connected in parallel between the negative input of U3 and the input side of resistor R7. The output from U3 is the signal P representative of the static pressure. This signal is provided to microcontroller 28.

High pass filter 46 receives the amplified pressure signal from amplifier circuit 42 by way of capacitors C5 and C6. Filter 46 is composed of series connected capacitors C7 (100uF) and C8 (100uF). These capacitors provide high pass filtering with a cutoff frequency of about 0.012Hz and remove the DC component in the pressure signal.

Low pass filter 48 presents a cutoff frequency of about 3.6 Hz and receives the high pass output from filter 46 at the positive input terminal of amplifier U4 (Type LT1078). Reference voltage at 2.5 V is also supplied to this terminal by way of resistor R8 (220K). Supply voltage at 6.2 V is connected to U4 with grounded capacitor C8 (0.1uF) also connected thereto. The output from U4 is connected to the negative input terminal thereof and also to the negative input terminal of amplifier U5 by way of resistor R9 (100K). Reference voltage at 2.5 V is connected by way of resistor R10 (253K) to the positive input terminal of U5. Feedback is provided from the output of U5 to the negative input terminal by way of parallel-connected, capacitor C10 (0.22uF) and resistor R11 (200K). The output from U5 is flow signal F representative of the air flow through conduit 16 and thereby representative of the respiration of a patient using apparatus 10.

Static pressure signal P and flow signal F are provided to microcontroller 28 (Motorola Type 68HC11) as analog signals on two channels. Microcontroller 28 includes an internal analog multiplexer for each channel, analog-to-digital converter, and logic processor with RAM and ROM. Microcontroller 28 provides output data to blower controller 18.

In operation, the respiration of a patient using apparatus 10 results in air flow through conduit 16 in both directions corresponding to inhalation and exhalation. This, in turn, causes varying pressure in probe 22 representative of the air flow including direction and magnitude and thereby representative of patient respiration. Pressure sensor 24 converts the varying pressure to an analog signal which is conditioned through filter 26 resulting in flow signal F. This signal presents a waveform representative of patient respiration.

A computer program stored in the ROM of microcontroller 28 directs the operation of microcontroller 28 for analyzing the waveform. In particular, the program would use high and low peak detect for each wave cycle and compare the peak-to-peak difference to an average of eight previous detected breaths. If the last peak-to-peak difference is greater than 40% of the average breath signal, then the breath is deemed valid and included in the new average. If the difference is less than 40% of the average, the breath signal is not included in the average. If no valid breath is detected for several seconds, then the apparatus is deemed not connected to the patient. The program also includes hysteresis and time delays to eliminate false peak-to-peak values and breath rates higher than reasonable maximum. The breath rate detection is limited to 60 breaths per minute and the minimum flow signal that can be detected reliably is about 30 liters per minute peak to peak.

If apparatus 10 is in use as indicated by the detection of valid breaths, then compliance data is stored representative of this condition. This compliance data can also include the time of day at which usage begins and ends, or the length of time that usage has occurred, or both. Additionally, the compliance data can include the static pressure as indicated by pressure signal P during the time of use. In preferred forms, the compliance data would be stored in memory 30 such as a nonvolatile, random access memory connected to microcontroller 28. In the alternative, compliance data could be forwarded to blower controller 18 for storage with other data.

Subsequently, the compliance data can be downloaded for the later study to determine whether the patient has complied with the prescribed use of apparatus 10. This can be an important factor in effective treatment. For example, if a patient is being treated for sleep apnea but exhibits continuing symptoms, the treatment prescriber might deduce that a higher airway pressure is needed. However, if the compliance data as provided by the present invention indicates that apparatus 10 has not been used consistently by the patient, then the higher prescribed pressure would not be the proper course of treatment.

Thus, the present invention provides an important means to improve treatment effectiveness. Moreover, the present invention enables this improvement by using only a single probe and sensor for sensing pressure and air flow, including both direction and magnitude, in conduit 16. Those skilled in the art will also appreciate that the present invention encompasses many variations in the preferred embodiment described herein. For example, the invention could be used for BiPAP and INAP systems. Having thus described the preferred embodiments of the present invention, the following is claimed as new and desired to be secured by Letters Patent:

What is claimed is:

1. In a positive airway pressure apparatus including a gas delivery unit operable to deliver pressurized gas to a patient's airway during successive patient breath cycles, a sensor operably connected with said unit and a controller coupled with said sensor, the improvement which comprises:

said sensor operable to measure a patient breath-indicating parameter selected from the group consisting of pressure, air flow direction and combinations thereof in said unit and to generate a sensor output corresponding to said parameter;

said output presenting high and low peaks during a breath; and said controller receiving said sensor output for analyzing the output to determine use or non-use of the apparatus by the patient as a function of said measured parameter and operable for analyzing said peaks and comparing said peaks to peak data representative of previous breaths of the patient for determining whether current high and low peaks are representative of an actual breath.

2. The apparatus of claim 1, said gas delivery unit including a blower unit, a nose mask configured for covering the nose of the patient, and a conduit interconnecting said blower unit with said nose mask, said blower unit delivering pressurized gas through said conduit, to said nose mask and thereby to the patient.

3. The apparatus of claim 2, further including a signal processor coupled with said sensor operable for receiving and analyzing said patient breath-indicating parameter for determining said air flow direction in said conduit, such being indicative of the patient's respiration and thereby the patient's use of said apparatus.

4. The apparatus of claim 3, said signal processor including a microcontroller operable for analyzing said signals to determine air flow magnitudes in said conduit and whether said magnitudes exceed predetermined limits in correspondence with said air flow direction, such being indicative of the patient's respiration and thereby the patient's use of said apparatus.

5. The apparatus of claim 4, said output presenting high and low peaks during a breath, said microcontroller operable for analyzing said peaks and comparing said peaks to peak data representative of previous breaths of the patient for determining whether current high and low peaks are representative of an actual breath.

6. The apparatus of claim 5, said peak data including the average of a previous plurality of detected breaths, said microcontroller operable for determining whether the peak-to-peak difference of a current breath exceeds a predetermined threshold of the average peak-to-peak difference of a plurality of previous breaths.

7. The apparatus of claim 6, said plurality of detected breaths including eight previously detected breaths, said threshold including 40%.

8. The apparatus of claim 1, said controller including a memory unit operable for storing said output and for subsequent retrieval thereof.

9. The apparatus of claim 8, said opposed probe end operatively coupled with said sensor and operable for sensing said varying pressure and for producing pressure signals representative thereof.

10. The apparatus of claim 12, said peak data including the average of a previous plurality of detected breaths, said controller operable for determining whether the peak-to-peak difference of a current breath exceeds a pre-determined threshold of the average peak-to-peak difference of a plurality of previous breaths.

11. The apparatus of claim 10, said plurality of detected breaths including eight previous detected breaths, said threshold including 40%.

12. The apparatus of claim 1, said output including the times during which said apparatus was used.

13. The apparatus of claim 1, said output including waveforms having peaks representative of a patient breath-indicating parameter and thereby representative of patient respiration.

14. The apparatus of claim 13, said controller including a computer program operable for directing said controller and analyzing said waveform.

15. The apparatus of claim 1, said output producing an analog air pressure signal corresponding to said patient breath-indicating parameter.

16. In a positive airway pressure apparatus including a gas delivery unit operable to deliver pressurized gas to a patient's airway during successive patient breath cycles, a sensor operably connected with said unit and a controller coupled with said sensor, the improvement which comprises:

said sensor operable to measure a patient breath-indicating parameter selected from the group consisting of pressure, air flow direction and combinations thereof in said unit and to generate a sensor output corresponding to said parameter;

said controller receiving said sensor output for analyzing the output to determine use or non-use of the apparatus by the patient as a function of said measured parameter;

said output including waveforms having peaks representative of a patient breath-indicating parameter and thereby representative of patient respiration;

said controller including a computer program operable for directing said controller and analyzing said waveform; and said program including high and low peak detect for said waveforms and operable for analyzing peak-to-peak differences to determine if said peaks are representative of actual patient breaths.

17. The apparatus of claim 16, said program including hysteresis and time delays operable for eliminating false peak-to-peak values.

18. The apparatus of claim 16, said program comparing said peak-to-peak differences to the average peak-to-peak difference of a plurality of previous patient breaths.

19. The apparatus of claim 18, said plurality including the average of at least eight previously detected breaths.

20. The apparatus of claim 19, wherein an actual patient breath is determined when said peak-to-peak difference is greater than 40% of said average.

21. In a positive airway pressure apparatus including a gas delivery unit operable to deliver pressurized gas to a patient's airway during successive patient breath cycles, a sensor operably connected with said unit, and a controller coupled with said sensor, the improvement which comprises:

said sensor operable to measure a patient breath-indicating parameter selected from the group consisting of pressure, air flow direction and combinations thereof in said unit and to generate a sensor output corresponding to said parameter;

said controller receiving said sensor output for analyzing the output to determine use or non-use of the apparatus by the patient as a function of said measured parameter;

said gas delivery unit including a blower unit and a conduit connected with said blower unit and adapted for coupling with a patient, said blower unit delivering pressurized gas through said conduit to the patient; and said sensor including a tubular probe having a probe tip positioned in said conduit and oriented within the confines of said conduit in order to intersect gas flow through the conduit, said probe having an opposed probe end, said probe tip configured for producing varying pressure in said probe that vary according to said air flow direction in said conduit.

22. The apparatus of claim 21, said probe tip further including an open end and an upstanding vane on one side thereof for producing a differential pressure across the probe tip in response to air flow thereacross and thereby for producing said varying pressure in response to varying air flow across said probe tip.

23. The apparatus of claim 21, said tubular probe configured to permit air flow between said probe tip and said opposed probe end.

* * * * *